(12) United States Patent
Pacheco et al.

(10) Patent No.: US 10,865,209 B2
(45) Date of Patent: Dec. 15, 2020

(54) PROCESS FOR PREPARING TEMOZOLOMIDE AND AN INTERMEDIARY

(71) Applicant: CRISTÁLIA PRODUTOS QUÍMICOS FARMACÊUTICOS LTDA, Itapira (BR)

(72) Inventors: Ogari Pacheco, Itapira (BR); Vincenzo De Sio, Itapira (BR); Murilo Massoni, Itapira (BR); Leandro Camargo, Itapira (BR)

(73) Assignee: CRISTÁLIA PRODUTOS QUÍMICOS FARMACÊUTICOS LTDA, Ponte Preta Cep (BR)

( * ) Notice: Subject to any disclaimer, the term of this patent is extended or adjusted under 35 U.S.C. 154(b) by 0 days.

(21) Appl. No.: 16/471,524

(22) PCT Filed: Dec. 19, 2017

(86) PCT No.: PCT/BR2017/050393
§ 371 (c)(1),
(2) Date: Jun. 19, 2019

(87) PCT Pub. No.: WO2018/112589
PCT Pub. Date: Jun. 28, 2018

(65) Prior Publication Data
US 2020/0190088 A1    Jun. 18, 2020

(30) Foreign Application Priority Data

Dec. 20, 2016  (BR) .......................... 1020160299454

(51) Int. Cl.
*C07D 487/04*    (2006.01)
(52) U.S. Cl.
CPC .................... *C07D 487/04* (2013.01)

(58) Field of Classification Search
CPC .................................................... C07D 487/04
USPC .......................................... 544/179; 514/183
See application file for complete search history.

(56) References Cited

U.S. PATENT DOCUMENTS

| | | |
|---|---|---|
| 5,260,291 A | 11/1993 | Lunt et al. |
| 6,844,434 B2 | 1/2005 | Kuo |
| 8,232,392 B2 | 7/2012 | Turchetta et al. |

FOREIGN PATENT DOCUMENTS

| | | |
|---|---|---|
| EP | 2151442 A2 | 2/2010 |
| WO | 2008038031 A1 | 9/2007 |
| WO | 2010140168 A1 | 12/2010 |

OTHER PUBLICATIONS

International Search Report and Written Opinion issued in corresponding International Application No. PCT/BR2017/050393 dated Dec. 19, 2017.
Duspara et al., "Synthesis and Reactivity of N-Alkyl Carbamoylimidazoles: Development of N-Methyl Carbamoylimidazole as a Methyl Isocyanate Equivalent", The Journal of Organic Chemistry, 2012, vol. 77, 7 pages.
Wang et al., "Antitumor Imidazotetrazines. 35. New Synthetic Routes to the Antitumor Drug Temozolomide", J. Org. Chem., 1997, vol. 62, No. 21, 7 pages.
Mishra et al.—Isocyanates Induces DNA Damage, Apoptosis, Oxidative Stress, and Inflammation in Cultured Human Lymphocytes; J Biochem Molecular Toxicology, vol. 22, No. 6, 2008; pp. 429-440.

*Primary Examiner* — Venkataraman Balasubramanian
(74) *Attorney, Agent, or Firm* — Roberts Calderon Safran & Cole P.C.

(57) ABSTRACT

The present invention relates to an efficient and industrially advantageous process for preparing temozolomide and the carbamoyl-AICA intermediate through the use of N-methyl carbamoylimidazole in a good overall yield and high purity.

21 Claims, 4 Drawing Sheets

PROCESS FOR PREPARING TEMOZOLOMIDE AND AN INTERMEDIARY

CROSS-REFERENCE TO RELATED APPLICATIONS

The present application is the U.S. National Phase of International Application PCT/BR2017/050393 filed on Dec. 19, 2017, claiming priority of Brazilian Patent Application No. BR1020160299454 filed Dec. 20, 2016.

The present invention relates to a process for preparing temozolomide and the carbamoyl-AICA intermediate through the use of N-methyl carbamoylimidazole.

Temozolomide, chemically known as 8-carbamoyl-3-methylimidazo[5,1-d]-1,2,3,5-tetrazin-4(3H)-one, is represented by structural formula I.

I

Temozolomide is a drug that exhibits antitumor activity and was first described in U.S. Pat. No. 5,260,291. This document describes a process, represented in Scheme 1, which comprises diazotising 5-aminoimidazole-4-carboxamide (AICA) with sodium nitrite in an acid medium, to obtain an intermediate diazonium salt, which is then treated with methyl isocyanate to obtain temozolomide.

Scheme 1

Such process has the following disadvantages: i) synthesis of a potentially explosive diazo (5-diazo-1H-imidazole-4-carboxamide) intermediate; (ii) use of methyl isocyanate, an explosive compound, highly toxic in admixture with air and, therefore, very dangerous handling, especially in a industrial scale; and iii) very time-consuming condensation reaction (about 20 days).

U.S. Pat. No. 6,844,434 describes a process for temozolomide preparation, as shown in Scheme 2 below, which comprises the reaction of AICA hydrochloride salt with 4-nitrophenyl chloroformate to provide a 4-nitrophenyl ester intermediate which subsequently reacts with methyl hydrazine to obtain the hydrazine intermediate, which is then cyclized to temozolomide.

Scheme 2

Although this route does not use methyl isocyanate, methylhydrazine is used, a potentially carcinogenic compound, and chloroformate, that is easily hydrolyzable, contributing to a low yield reaction.

International application WO2008038031 describes a temozolomide preparation with subsequent diazotization and cyclization of the carbamoyl-AICA intermediate in the presence of metal halide excess, e.g., lithium bromide or chloride, an acid and a nitrous acid source, without hydrazine intermediate formation. According to this document, carbamoyl-AICA may be prepared from AICA hydrochloride salt, via 4-nitrophenyl ester intermediate, as described in J. Org. Chem. 1997, 62, 7288-7294. The complete process is shown below in Scheme 3.

Temozolomide is isolated from the acid solution by countercurrent extraction using continuous liquid-liquid extractor which requires large volumes of solvents, such as dichloromethane. The use of large quantities of metal halide, of a special apparatus (extractor) and large volumes of dichloromethane makes the process in general expensive, non-competitive and unfeasible from an industrial and environmental point of view.

The first step comprises the preparation of carbamoyl-AICA intermediate from AICA base reaction with N-suc- Scheme 3

The U.S. Pat. No. 8,232,392 patent describes a synthesis of temozolomide in two steps, according to Scheme 4 below.

Scheme 4 cinimidyl-N'-methyl carbamate in the presence of diisopropylethylamine (DIPEA) and acetonitrile (ACN).

In the second step, temozolomide is prepared according to the description in J. Org. Chem. 62, 7288-7294 (1997). The transformation of carbamoyl-AICA into temozolomide occurs through carbamoyl-AICA diazotization in the presence of sodium nitrite and tartaric acid. At the end of this reaction, a mixture of about 50:50 temozolomide and azahypoxanthine by-product is obtained. Temozolomide is purified through a XAD 1600 chromatographic column filled with adsorbent polymer resin.

The use of DIPEA base, a compound considered to be hazardous because it is highly flammable and toxic by inhalation, and the reaction time of about 16 hours to form carbamoyl-AICA, make this process disadvantageous to the industry.

International application WO2010140168 also describes the temozolomide synthesis in two steps, according to Scheme 5 below, however carbamoyl-AICA is prepared from amino cyanoacetamide condensation reaction with a urea compound, 1-methyl-3-carbamoyliminomethyl urea, in the presence of an acid in an alcoholic solvent, such as methanol, by a slow process which takes about 18 hours to complete reaction.

Scheme 5

[Chemical structures: Urea compound + amino cyanoacetamide → Carbamoyl-AICA → Temozolomide]

Clearly, there is a need to develop a safer and more efficient and industrially advantageous process for preparing temozolomide and carbamoyl-AICA, a key intermediate in the preparation of temozolomide.

The present invention satisfies technique's need as it avoids the use of hazardous reagents, such as methyl isocyanate, methylhydrazine and DIPEA, providing an improved process, industrially feasible and advantageous for preparing temozolomide and carbamoyl-AICA intermediate with a good overall yield and high purity.

SUMMARY OF THE INVENTION

The present invention relates to a process for preparing temozolomide according to Scheme 6 below.

Scheme 6

[Chemical structures: AICA base + N-methylcarbamoyl imidazole → Carbamoyl-AICA → Temozolomide]

The process comprises the following steps:

a) Reacting AICA base with N-methyl carbamoylimidazole to provide carbamoyl-AICA;

b) Reacting carbamoyl-AICA with an alkali metal or alkaline earth metal nitrite in the presence of an acid to provide temozolomide.

According to the process of the present invention, the carbamoyl-AICA intermediate is prepared from the AICA base reaction with N-methyl carbamoylimidazole. This reaction is carried out in an aprotic polar organic solvent. Preferably, the solvent is acetonitrile or tetrahydrofuran, more preferably acetonitrile. Carbamoyl-AICA thus obtained undergoes consecutive diazotization and cyclization to obtain temozolomide in the presence of an alkali or alkaline earth metal nitrite and an acid. Preferably, the alkali metal nitrite is sodium nitrite and the acid is tartaric acid. Temozolomide is purified with subsequent crystallization. Preferably, temozolomide is purified through a chromatographic column filled with adsorbent polymer resin, and subsequent crystallization.

The N-methyl carbamoylimidazole compound employed for carbamoyl-AICA preparation can be commercially purchased or prepared from the carbonyldiimidazole reaction with methylamine hydrochloride in the presence of a solvent mixture consisting of acetonitrile and dimethylformamide.

According to another aspect of the present invention, there is provided a process for preparing temozolomide according to Scheme 7 below:

Scheme 7

[Chemical structures: carbonyldiimidazole + CH₂NH₂·HCl (methylamine hydrochloride) → N-methylcarbamoyl imidazole; AICA base]

Temozolomide        Carbamoyl-AICA

The process comprises the following steps:
(a) Reacting carbonyldiimidazole with methylamine hydrochloride in a mixture of acetonitrile and dimethylformamide to obtain N-methylcarbamoylimidazole;
(b) Reacting AICA base with N-methyl carbamoylimidazole in an aprotic polar organic solvent to provide carbamoyl-AICA;
(c) Reacting carbamoyl-AICA with sodium nitrite, added to the reaction medium in solid form, in the presence of a tartaric acid solution and, at the end of the reaction, heat the reaction mixture to 60° C. and filter to provide temozolomide and azahypoxanthine in a ratio of 60:40;
(d) Purifying temozolomide through a chromatographic column filled with adsorbent polymer resin, containing a carbon capsule coupled to the end of the column, to provide a clarified temozolomide solution and subsequent crystallization.

According to another aspect of the present invention, there is provided a process for preparing carbamoyl-AICA key intermediate comprising the reaction between AICA base and N-methyl carbamoylimidazole in an aprotic polar organic solvent. Preferably, the solvent is acetonitrile or tetrahydrofuran, more preferably acetonitrile.

Temozolomide and carbamoyl-AICA are obtained in good overall yield and high purity. Temozolomide is obtained with purity greater than 99.98% and carbamoyl-AICA with purity of 99.20% (both by HPLC).

DESCRIPTION OF THE DRAWINGS

The following is a description of the drawings accompanying this report, for illustration of the present invention.

DETAILED DESCRIPTION OF THE INVENTION

The present invention relates to an efficient and industrially advantageous process for preparing temozolomide, as shown in Scheme 6 above.

The process comprises the following steps:
(a) Reacting AICA base with N-methyl carbamoylimidazole to provide carbamoyl-AICA;
(b) Reacting carbamoyl-AICA with an alkali metal or alkaline earth metal nitrite in the presence of an acid to provide temozolomide.

The process begins with the reaction of AICA base with N-methyl carbamoylimidazole to provide the carbamoyl-AICA key intermediate. This reaction is carried out in an aprotic polar organic solvent, preferably acetonitrile or tetrahydrofuran, more preferably acetonitrile. This reaction occurs at a temperature between 55° C. and 60° C. for about 3 to 6 hours. The reaction mixture is then cooled to between 0° C. and 5° C. and after two hours the carbamoyl-AICA crystals are isolated by filtration.

According to the present invention, the carbamoyl-AICA preparation from the reaction between N-methyl carbamoylimidazole and AICA base does not require the addition of DIPEA base. However, the in situ formed imidazole functions as a base that drive the reaction towards the desired product more safely and rapidly, as compared to the process described in Example 1 of EP2151442, the reaction time of which is about 16 hours.

The carbamoyl-AICA conversion to temozolomide may be carried out according to the description in *J. Org. Chem.* 62, 7288-7294 (1997). In this case, the carbamoyl-AICA diazotization and cyclization reaction is performed in the presence of an aqueous solution of sodium nitrite and tartaric acid at 0° C. At the end of the reaction, a mixture comprising temozolomide and a by-product called azahypoxanthine is obtained in a ratio of approximately 50:50.

Preferably, according to the process of the present invention, the conversion reaction of carbamoyl-AICA to temozolomide is carried out in the presence of an alkali or alkaline earth metal nitrite and an acid according to the illustration of Scheme 8 below, which incorporates improvements in relation to the prior art. Preferably, the alkali metal nitrite is sodium nitrite and the acid is tartaric acid.

To a carbamoyl-AICA aqueous solution is added sodium nitrite in solid form, the reaction medium temperature being held at 0° C. Then a tartaric acid solution is slowly added to the reaction medium in order to avoid an exothermic reaction, which could lead to decomposition products formation. The reaction mixture is stirred for 2 hours at 0° C., followed by a further 2 hours stirring at room temperature. After the consecutive carbamoyl-AICA diazotization and cyclization, the reaction mixture is heated to a temperature between 60° C. and 65° C., preferably 60° C., and the obtained suspension is filtered, preferably through Buchner funnel providing a solution containing temozolomide and the by-product azahypoxanthine in a ratio of 60:40.

Scheme 8

-continued

Pure Temozolomide     Temozolomide     Azahypoxanthine Surprisingly, the rise in temperature between 60° C. and 65° C., after diazotization and cyclization, according to the present invention, favors: i) the suspension filtration ii) the conversion of the transitory intermediate to azahypoxanthine; iii) the increase in the ratio of temozolomide to azahypoxanthine that goes from 50:50 to 60:40; iv) the chromatography purification of temozolomide with an effective separation between temozolomide and azahypoxanthine; v) the overall yield of temozolomide.

Accordingly, the process of the present invention further comprises the purification of temozolomide and subsequent crystallization. Preferably, temozolomide is purified through a chromatographic column filled with adsorbent polymer resin, and subsequent crystallization.

The solution containing 60% temozolomide and 40% azahypoxanthine is acidified to pH 2-3 with an inorganic acid, such as hydrochloric acid, sulfuric acid, etc., preferably hydrochloric acid. The resulting acidic solution of temozolomide is purified through a chromatographic column filled with adsorbent polymer resin under mobile phase elution containing a mixture of acidified water and ethanol. The obtained eluate is filtered through a carbon capsule coupled to the end of the chromatographic column to provide a clarified temozolomide solution with a purity greater than 90% (HPLC analysis) which is subsequently crystallized to achieve high purity, above 99.98% by HPLC.

Examples of adsorbent polymer resins are: amberlites XAD 1600 and XAD 1180, both from Rohm and Haas; and the Mitsubish HP20L, HP 2055 and SP825.

The N-methyl carbamoylimidazole compound employed in step (a) of the process of the present invention may be commercially purchased or prepared as described in J. Org. Chem. 2012, 77(22), 10362-10368 from the reaction of carbonyldiimidazole with methylamine hydrochloride in the presence of a solvent mixture consisting of acetonitrile and dimethylformamide. However, its use in temozolomide or in carbamoyl-AICA intermediate preparation has not been described in the art until the present date.

N-methyl carbamoylimidazole has the advantage of being a stable crystalline solid, have low toxicity, it is non-explosive, easily stored and cheap, capable of reacting with AICA base very effectively to provide carbamoyl-AICA, a key intermediate for the preparation of temozolomide, as demonstrated in the present invention.

According to another aspect of the present invention, there is provided a process for preparing temozolomide comprising the following steps:
(a) Reacting carbonyldiimidazole with methylamine hydrochloride in a mixture of acetonitrile and dimethylformamide to obtain N-methylcarbamoylimidazole;
(b) Reacting AICA base with N-methyl carbamoylimidazole in an aprotic polar organic solvent to provide carbamoyl-AICA;
(c) Reacting carbamoyl-AICA with sodium nitrite, added to the reaction medium in solid form, in the presence of a tartaric acid solution and, at the end of the reaction, heat the reaction mixture to 60° C. and filter to provide temozolomide and azahypoxanthine in a ratio of 60:40;
(d) Purifying temozolomide through a chromatographic column filled with adsorbent polymeric resin, containing a carbon capsule coupled to the end of the column, to provide a clarified temozolomide solution and subsequent crystallization.

The process starts from the reaction between carbonyldiimidazole and methylamine hydrochloride in a mixture of acetonitrile and dimethylformamide in the volume/volume ratio of 3:1, at room temperature for 2 hours. Then the resulting solution is concentrated to remove the acetonitrile solvent. In addition, N-methyl carbamoylimidazole is purified by silica column chromatography under elution in a mixture of methanol and 3% dichloromethane. The fraction with the purified product is concentrated to the residue and the obtained solid is dried.

In the second step of the process, AICA base reacts with N-methyl carbamoylimidazole in an aprotic polar organic solvent to provide the carbamoyl-AICA key intermediate. Preferably, the solvent is acetonitrile or tetrahydrofuran, more preferably acetonitrile. This reaction takes place at a temperature between 55° C. and 60° C., for about 3 to 6 hours. The reaction mixture is then cooled to between 0° C. and 5° C. and, after two hours, the carbamoyl-AICA crystals are isolated by filtration.

The steps of carbamoyl-AICA conversion to temozolomide (diazotization and cyclization) and purification by chromatographic column are performed as described in Scheme 8 above.

To a carbamoyl-AICA aqueous solution is added sodium nitrite in solid form, the temperature of the reaction medium being held at 0° C. Then a solution of tartaric acid is slowly added to the reaction medium in order to avoid an exothermic reaction, which could lead to the decomposition products formation. The reaction mixture is stirred for 2 hours at 0° C., followed by a further 2 hours stirring at room temperature. After the consecutive diazotization and cyclization of carbamoyl-AICA, the reaction mixture is heated to a temperature between 60° C. and 65° C., preferably 60° C., and the obtained suspension is filtered, preferably through Buchner funnel providing a solution containing temozolomide and the by-product azahypoxanthine in a ratio of 60:40.

The solution containing 60% temozolomide and 40% azahypoxanthine is acidified to pH 2-3 with an inorganic acid, such as hydrochloric acid, sulfuric acid, etc., preferably hydrochloric acid. The resulting acidic solution of temozolomide is purified through a chromatographic column filled with adsorbent polymer resin under mobile phase elution containing a mixture of acidified water and ethanol. The obtained eluate is filtered through a carbon capsule coupled to the end of the chromatographic column to provide a clarified temozolomide solution with a purity greater than 90% (HPLC analysis) which is subsequently crystallized to achieve high purity, above 99.98% by HPLC.

The clarified temozolomide solution, after said chromatography, is then concentrated at 60° C. and 25 mbar to between 30 and 40 volumes relative to the theoretical weight of temozolomide, providing a suspension that is cooled to 5-10° C., kept under stirring for 2 h and filtered. The collected solid is washed and dried. The crystalline form of temozolomide obtained under these conditions is monohydrate, characterized by an X-ray diffraction pattern (XRD) and Infrared Spectrum (IR) according to the graphs respectively shown in FIGS. 1 and 2. The reaction conditions are described in detail in Example 4.

Alternatively, the clarified temozolomide solution, after said chromatography, is then concentrated at 60° C. and 25 mbar up to about 5 volumes relative to the theoretical weight of temozolomide, providing a suspension that is combined with 15 volumes of acetone. The mixture is refluxed for 1 h and the obtained suspension is cooled to 5° C., kept under stirring for 2 h and filtered. The collected solid is washed and dried. The crystalline form of temozolomide obtained under these conditions is form III, characterized by an X-ray diffraction pattern (XRD) and Infrared Spectrum (IR) according to the graphs respectively shown in FIGS. 3 and 4. The reaction conditions are described in detail in Example 5.

In addition, temozolomide monohydrate prepared according to the process of the present invention can be converted to temozolomide Form III (Examples 6 and 7). A suspension of temozolomide monohydrate in a mixture 1:3 ratio (volume/volume) of water and acetone is heated to 60° C. and stirred for 0.5 hour. The quasi-solution is cooled to room temperature for 1 h and then to between 0° C. and 5° C., and filtered. The collected solid is washed and dried to provide temozolomide form III.

In another aspect of the present invention, there is provided a process for preparing carbamoyl-AICA key intermediate comprising N-methyl carbamoylimidazole reaction with AICA base in an aprotic polar organic solvente, such as acetonitrile or tetrahydrofuran. Preferably, the solvent is acetonitrile.

The processes of the present invention overcome state-of-the-art problems by providing simple, economical, robust and industrially advantageous synthetic routes to obtain purified temozolomide and to the carbamoyl-AICA key intermediate in high yield and purity.

The following examples are merely illustrative and should be employed for a better understanding of the claimed processes, but should not be used in order to limit the scope of the present invention.

Example 1

Preparation of N-methyl carbamoylimidazole 7.17 g of carbonyldiimidazole, 2.70 g of methylamine hydrochloride, 24 ml of acetonitrile (ACN) and 8 ml of dimethylformamide (DMF) were kept under stirring for 2 hours at room temperature. After 2 hours, the clear yellow solution obtained was concentrated under reduced pressure at 40° C. to remove ACN. The resulting oil was purified through a silica column in a mixture of methanol and dichloromethane 3% and the fraction containing the purified product was concentrated to residue under vacuum at 30° C. to provide 4.1 g of N-methyl carbamoylimidazole as a white solid (75% yield).

Melting point=113-115° C.; $^1$H NMR (400 MHz, CDCl$_3$) δ 8.14 (brs, 1H), 7.38 (t, 1H), 7.12 (brs, 1H), 6.95 (s, 1H), 3.23 (d, 3H); $^{13}$C NMR (100 MHz, CDCl$_3$) δ 150.1, 137.1, 131.4, 117.2 e 28.2.

Example 2

Preparation of Carbamoyl-AICA

To a suspension of AICA base, 20.0 g in 100 mL of acetonitrile, was heated at 55-60° C. and 30 g of N-methylcarbamoylimidazole was added. The reaction mixture was maintained at 55-60° C. for 6 hours and then cooled to 0-5° C. After 2 hours, the resulting suspension was filtered and washed with precooled water. The obtained crystals were dried under vacuum at 50° C. for 6 hours, yielding 23.0 g of carbamoyl-AICA as a white solid (80% yield and 99.2% HPLC purity). $^1$H NMR (500 MHz, DMSO): δ 2.84 (d, 3H); 2.50-2.52 (DMSO); 3.35 (H$_2$O); 6.38 (s, 2H); 6.85 (d, 2H); 7.61 (s, 2H); 8.42 (s, 2H). $^{13}$C (NMR, 125 MHz, DMSO) δ 26.9; 39.2-40.5 (DMSO); 111.6; 126.5; 143.8; 151.1; 166.7; IR (ATR, cm$^{-1}$): $v_{max}$ 3458; 3404; 3348; 3319; 3130; 3068; 2949; 1714; 1645; 1595; 1556; 1530; 1503; 1460; 1452; 1420; 1298; 1248; 1221; 1173; 1076; 955; 827; 745; 698; MS (ESI) Calculated to [C$_6$H$_9$N$_5$O$_2$+Na]$^+$=m/z 206.0648; found m/z=206.0645.

Example 3

Preparation of Carbamoyl-AICA

To a suspension of AICA base, 1.0 g in 6 mL of tetrahydrofuran, was heated at 55-60° C. and 1.5 g of N-methylcarbamoylimidazole was added. The reaction mixture was maintained at 55-60° C. for 6 hours and then cooled to 0-5° C. After 2 hours, the resulting suspension was filtered and washed with precooled water. The obtained crystals were dried under vacuum at 50° C. for 6 hours, yielding 0.8 g carbamoyl-AICA as a white solid (65% yield and 95.0% HPLC purity).

Example 4

Preparation of Temozolomide Monohydrate 500 mL of water and 40 g of carbamoyl-AICA were added in a 2 liter reactor. The reaction mixture was cooled to 0° C. and 15.8 g of sodium nitrite was added. The resulting mixture was stirred for 20 minutes and then a solution of tartaric acid (34 g in 100 mL of water) was added slowly. The reaction mixture was stirred for 2 h at 0° C. and then stirred at room temperature for 2 hours. The temperature was adjusted to 60° C., and the suspension was filtered and the residue washed with hot water. The filtrate containing 60% temozolomide and 40% azahypoxanthine was acidified to pH 2-3, eluted through a resin with acidified aqueous solution and ethanol. The eluate was clarified through a carbon filter coupled to the column outlet, obtaining a solution of temozolomide with purity greater than 90% (HPLC). The obtained solution was concentrated at 60° C. and 25 mbar to between 30 and 40 volumes relative to the theoretical weight of temozolomide to achieve a suspension with fine crystals. The suspension was then cooled to 5-10° C., stirred for 2 hours and filtered through Buchner funnel.

Figure 1:
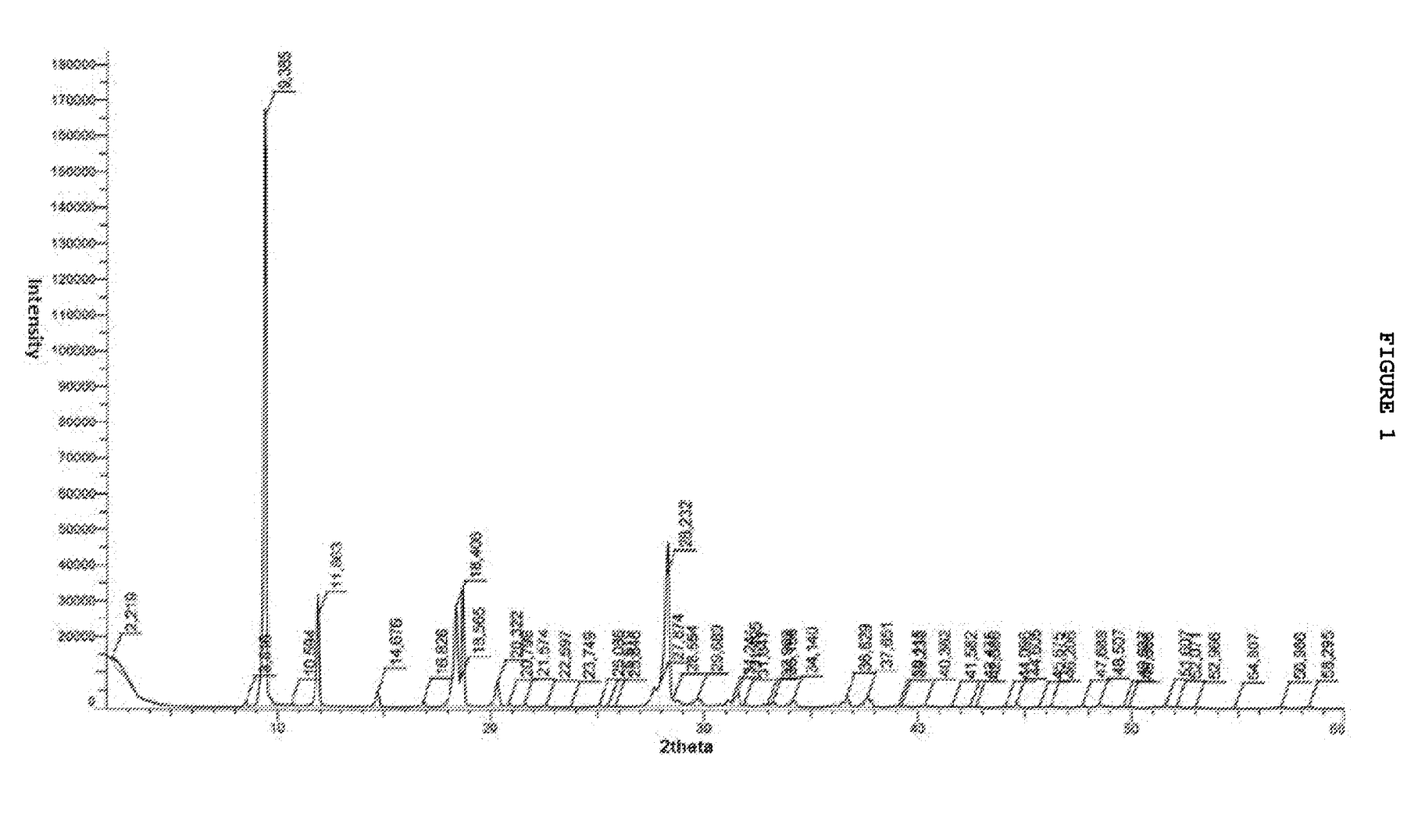
FIG. 1: PDRX for temozolomide monohydrate.
Figure 2:
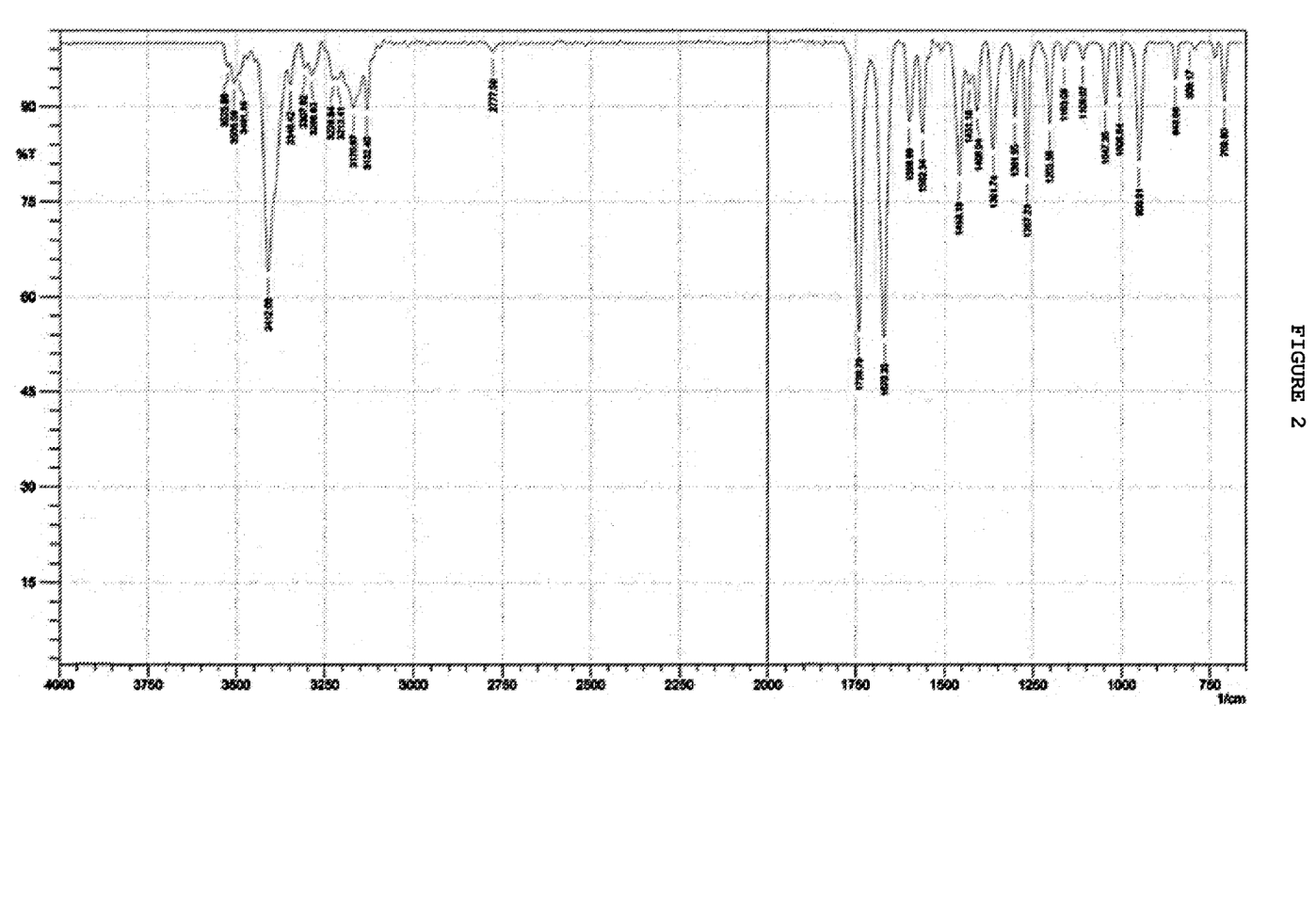
FIG. 2: IR (KBr) for temozolomide monohydrate.

The residue was washed with acidified water, and the collected crystals were dried under vacuum at 50° C. for 4 hours, providing 20 g of temozolomide monohydrate as a white solid of 99.98% purity (HPLC) e 47% yield. DRXP (2θ): 9.385, 11.863; 14.676; 16.826; 18.406; 18.565; 20.322; 28.232±0.2° (FIG. 1). IR (cm$^{-1}$) 3421; 3348; 1739; 1670; 1598; 1562; e 1408 (FIG. 2).

Example 5

Figure 3:
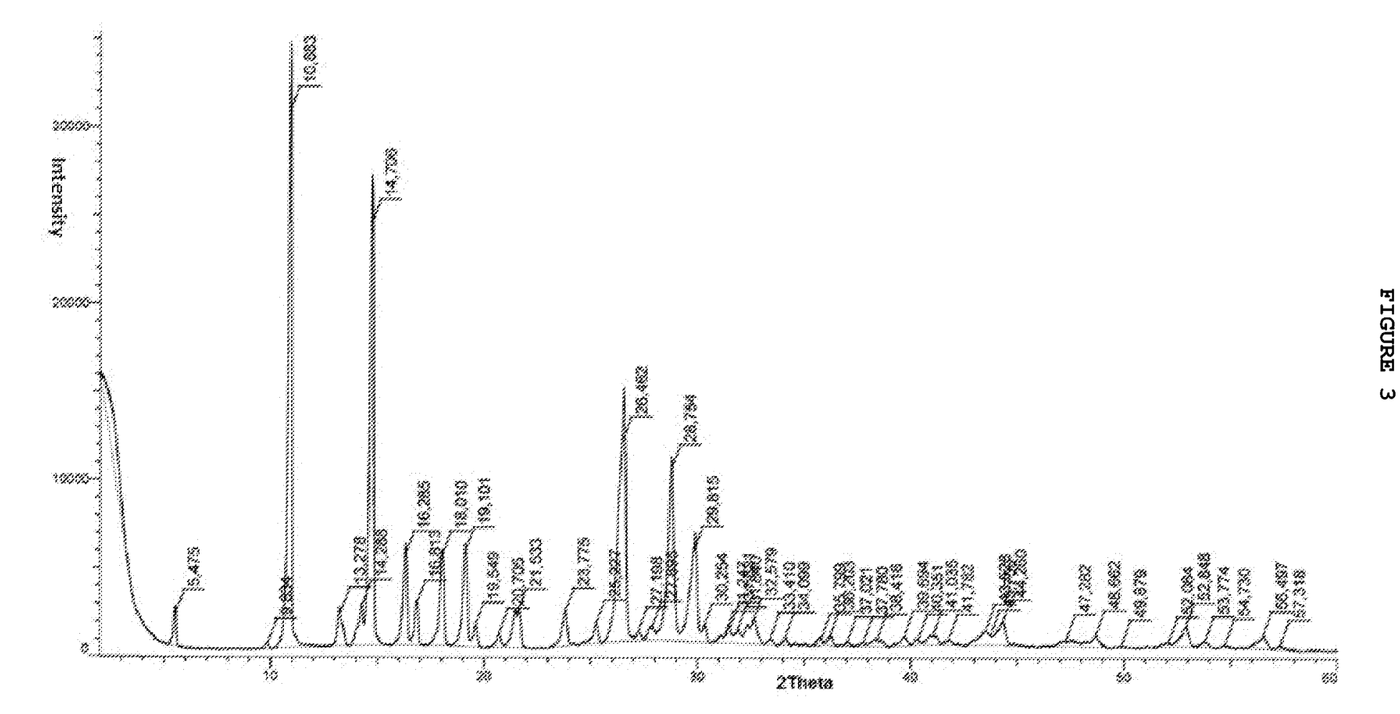
FIG. 3: PDRX for temozolomide form II.
Figure 4:
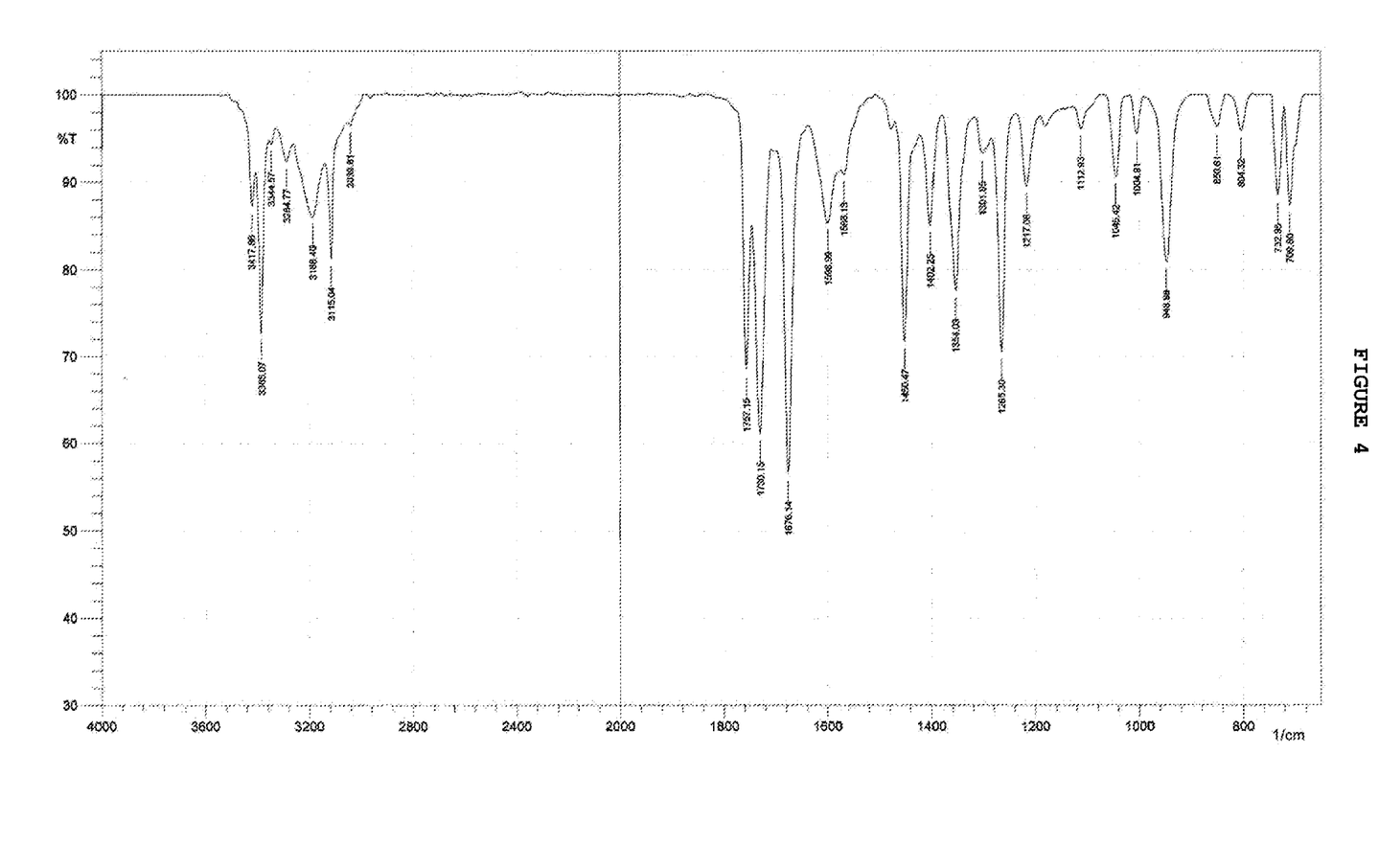
FIG. 4: IR (KBr) for temozolomide form III.

Preparation of Temozolomide Form III 250 mL of water and 20 g of carbamoyl-AICA were added in a 2 L reactor under stirring (250 rpm). The reaction mixture was cooled to 0° C. and 7.92 g of sodium nitrite were added to the reaction mixture which was stirred for 20 min. A solution of tartaric acid (17 g in 50 mL) was slowly added to the reaction mixture, which was kept under stirring for 2 h at 0° C. and then, at room temperature for a further 2 hours. The temperature was raised to 60° C. and the suspension was filtered through Buchner funnel and the residue washed with hot water. The filtrate containing 60% temozolomide and 40% azahypoxanthine was acidified to pH 2.2 with 18.5% HCl and eluted through Amberlite XAD 1600 resin with a flow of 1.2 BV/hr with a solution of acidified water and ethanol. The eluate was clarified through a carbon filter coupled to the column outlet, obtaining a solution of temozolomide with purity greater than 90% (HPLC). The solution obtained was concentrated at 60° C. and 25 mbar to 5 volumes relative to the theoretical temozolomide weight to obtain a suspension. 15 volumes of acetone were added to the suspension and the mixture was heated to reflux. After 1 hour, the suspension was cooled to 5° C., stirred for 2 h and filtered. The residue was washed 2 times with an acidified aqueous solution and acetone (1:3), and the resulting solid was dried under vacuum at 50° C. for 4 hours, providing 8 g of temozolomide form III in 99.99% purity (HPLC) and 38% yield. DRXP (2θ): 5.509; 10.909; 13.308; 14.725; 16.325; 16.836; 18.033; 19.122; 19.582; 20.725; 21.560; 23.806; 25.235; 26.480; 28.765; 29.843±0.2° (FIG. 3). IR (cm$^{-1}$): 3417; 3385; 1757; 1730; 1676; 1598; 1568 e 1402 (FIG. 4).

Example 6

Preparation of Temozolomide Form III

In a 2 L reactor, 246 ml of acetone (15 volumes) and 82 ml of water (5 volumes) were added to 16.4 g of temozolomide monohydrate at room temperature. The suspension was heated to 60° C. and stirred for 30 min. The resulting suspension (quasi-solution) was cooled to room temperature for 1 h and then at 0-5° C. for 1 h. After 2 hours, the suspension was filtered and the collected solid was washed twice with 50 mL of acetone and dried at 45° C. and 25 mbar for 5 h, giving 12.7 g of temozolomide form III (77.0% yield, 99.99% purity). RDXP (2θ): 5.475; 10.883; 13.278; 14.706; 16.285; 16.813; 18.010; 19.101; 19.549; 20.705; 21.533; 23.775; 25.227; 26.462; 28.754; 29.815±0.2°. IR (cm$^{-1}$): 3417, 3385, 1757, 1730, 1676, 1598, 1568, 1402.

Example 7

Preparation of Temozolomide Form III

In a 100 mL reactor, 18 mL of acetone (9 volumes) and 6 mL of water (3 volumes) were added to 2.0 g of temozolomide monohydrate at room temperature. The suspension was heated to 60° C. and kept under stirring for 30 min. The resulting suspension (quasi-solution) was cooled to room temperature for 1 h and then cooled to 0-5° C. for 1 h. After 2 hours, the suspension was filtered and the residue washed twice with 2 mL of acetone. The solid is dried at 45° C. and 25 mbar for 5 h, giving 1.64 g of temozolomide form III (82.0% yield, 99.99% purity). DRXP (2θ): 5.512; 10.923; 13.323; 14.739; 16.328; 16.848; 18.048; 19.128; 19.585; 20.727; 21.569; 23.812; 25.254; 26.491; 28.779; 29.849±0.2°. IR (cm$^{-1}$): 3417, 3385, 1757, 1730, 1676, 1598, 1568 e 1402.

The invention claimed is:

1. A process for preparing temozolomide, comprising the following steps:
   (a) Reacting AICA base with N-methyl carbamoylimidazole to provide carbamoyl-AICA;
   (b) Reacting carbamoyl-AICA with an alkali or alkaline earth metal nitrite in the presence of an acid to provide temozolomide.

2. The process according to claim 1, wherein step (a) is carried out in an aprotic polar organic solvent.

3. The process according to claim 2, wherein the solvent is acetonitrile or tetrahydrofuran.

4. The process according to claim 3, wherein the solvent is acetonitrile.

5. The process according to claim 1, wherein the alkali metal nitrite in step (b) is sodium nitrite added to the reaction medium in solid form.

6. The process according to claim 1, wherein the acid in step (b) is tartaric acid.

7. The process according to claim 1, which further comprises purifying temozolomide from the reaction (b), and crystallizing the temozolomide.

8. The process according to claim 1, wherein the N-methyl carbamoylimidazole of step (a) is prepared from the reaction of carbonyldiimidazole with methylamine hydrochloride in a mixture of acetonitrile and dimethylformamide.

9. A process for preparing temozolomide, comprising the following steps:
   (a) Reacting carbonyldiimidazole with methylamine hydrochloride in a mixture of acetonitrile and dimethylformamide to obtain N-methylcarbamoylimidazole;
   (b) Reacting AICA base with N-methyl carbamoylimidazole in an aprotic polar organic solvent to provide carbamoyl-AICA;
   (c) Reacting carbamoyl-AICA with sodium nitrite, added to the reaction medium in solid form, in the presence of a tartaric acid solution and, at the end of the reaction, heating the reaction mixture to 60° C. and filtering to provide temozolomide and azahypoxanthine in a ratio of 60:40;
   (d) Purifying temozolomide through a chromatographic column filled with adsorbent polymer resin containing a carbon capsule coupled to the end of the column to provide a clarified solution of temozolomide, and crystallizing temozolomide from the clarified solution.

10. The process according to claim 9, wherein the aprotic polar organic solvent in step (b) is acetonitrile or tetrahydrofuran.

11. The process according to claim 10, wherein the solvent is acetonitrile.

12. The process according to claim 9, wherein, after said chromatography in step (d), the clarified temozolomide solution is concentrated at 60° C. to between 30 and 40 volumes relative to the theoretical weight of temozolomide, and thereafter cooled to provide crystals of temozolomide monohydrate.

13. The process according to claim 9, wherein after said chromatography in step (d), the clarified temozolomide solution is concentrated at 60° C. to up to about 5 volumes relative to the theoretical weight of temozolomide, combined with 15 volumes of acetone, and thereafter cooled to provide crystals of temozolomide form III.

14. The process according to claim 12, wherein the temozolomide monohydrate is optionally suspended in a 1:3 ratio mixture of water and acetone, heated to 60° C. and then cooled to provide temozolomide form III.

15. A process for preparing carbamoyl-AICA comprising the reaction between AICA base and N-methyl carbamoylimidazole in an aprotic polar organic solvent.

16. The process according to claim 15, wherein the solvent is acetonitrile or tetrahydrofuran.

17. The process according to claim 16, wherein the solvent is acetonitrile.

18. The process according to claim 1, wherein the step (a) is performed without the addition of a tertiary amine base.

19. The process according to claim 9, wherein the step (b) is performed without the addition of a tertiary amine base.

20. The process according to claim 15, wherein the reaction is performed without the addition of a tertiary amine base.

21. The process according to claim 1, further comprising, at the end of the reaction, raising the temperature of the reaction mixture (b) to from 60° C. to 65° C.

\* \* \* \* \*